United States Patent
Wyatt (10) Patent No.: US 7,912,736 B2
(45) Date of Patent: Mar. 22, 2011

(54) METHOD AND A SYSTEM FOR OPTIMIZING HOSPITAL BEDS AND AMBULANCE ALLOCATIONS VIA A COMPUTER NETWORK

(76) Inventor: Phil Wyatt, Lake Forest, IL (US)

( * ) Notice: Subject to any disclaimer, the term of this patent is extended or adjusted under 35 U.S.C. 154(b) by 2151 days.

(21) Appl. No.: 10/880,230

(22) Filed: Jun. 29, 2004

(65) Prior Publication Data

US 2004/0243446 A1 Dec. 2, 2004

Related U.S. Application Data

(63) Continuation of application No. 09/544,508, filed on Apr. 6, 2000.

(51) Int. Cl.
*G06Q 10/00* (2006.01)
*G06Q 50/00* (2006.01)
*G06Q 40/00* (2006.01)
*A61B 5/00* (2006.01)
*G06F 19/00* (2006.01)

(52) U.S. Cl. ................................ 705/3; 705/2; 705/4
(58) Field of Classification Search .................. 705/2, 3, 705/4
See application file for complete search history.

(56) References Cited

U.S. PATENT DOCUMENTS

| | | | |
|---|---|---|---|
| 4,135,241 A | | 1/1979 | Stanis et al. |
| 5,748,907 A | * | 5/1998 | Crane ................................ 705/2 |
| 5,760,704 A | * | 6/1998 | Barton et al. ............ 340/825.49 |
| 5,867,821 A | * | 2/1999 | Ballantyne et al. ................ 705/2 |
| 5,940,834 A | | 8/1999 | Pinard et al. |
| 5,991,730 A | * | 11/1999 | Lubin et al. ........................ 705/3 |
| 5,995,937 A | | 11/1999 | DeBusk et al. |
| 6,000,000 A | * | 12/1999 | Hawkins et al. .............. 707/201 |
| 6,014,432 A | * | 1/2000 | Modney .................... 379/106.02 |
| 6,076,166 A | * | 6/2000 | Moshfeghi et al. ............... 726/4 |
| 6,192,382 B1 | * | 2/2001 | Lafer et al. ...................... 715/513 |
| 6,211,790 B1 | * | 4/2001 | Radomsky et al. ........ 340/573.4 |
| 6,289,088 B1 | | 9/2001 | Bruno et al. |
| 6,305,605 B1 | * | 10/2001 | Goetz et al. .................... 235/385 |
| 6,356,874 B1 | | 3/2002 | Ohrn |

* cited by examiner

*Primary Examiner* — Gerald J. O'Connor
*Assistant Examiner* — Amber Altschul
(74) *Attorney, Agent, or Firm* — Patents+TMS, P.C.

(57) ABSTRACT

A method and a system for optimizing hospital beds and ambulance allocations via a computer network are provided. The method and the system determine the status of emergency rooms and/or the status of beds in emergency rooms of hospitals via a computer network. The system and the method allocate emergency rooms and/or the beds in the emergency rooms of the hospitals to ambulances and/or ambulance services. The system and the method diverts or bypasses patients to emergency rooms of other hospitals for medical treatment.

20 Claims, 4 Drawing Sheets

METHOD AND A SYSTEM FOR OPTIMIZING HOSPITAL BEDS AND AMBULANCE ALLOCATIONS VIA A COMPUTER NETWORK

This application is a Continuation-In-Part application of co-pending U.S. patent application Ser. No. 09/544,508 filed on Apr. 6, 2000.

BACKGROUND OF THE INVENTION

The present invention generally relates to a method and a system for optimizing hospital beds and ambulance allocations via a computer network. More specifically, the present invention generally relates to a method and a system for determining the status of beds in hospitals via a computer network. Further, the present invention relates to a method and a system for determining the status of the beds in a rooms, such as, for example, emergency rooms of the hospitals. The system and the method may alert ambulance services of the status of the beds and/or the status of the rooms in the hospitals via the computer network. The ambulance services may transport and/or may deliver a patient to one of the hospitals based on the status of the beds and/or the status of the rooms in the hospital. Still further, the hospitals may update the computer network to reflect the current status of the beds and/or the rooms in the hospitals. Moreover, the ambulances may update the computer network to inform others as to the hospital receiving the patent.

It is, of course, generally known to provide databases having information thereon. The information may be stored within the database for accessing the information at a later time. Further, it is generally known to provide access to databases on a computer network, such as, for example, the internet. A website may be utilized to simultaneously provide access to the database for adding information to the database and for retrieving information from the database.

Known methods of moving patients to beds in medical health facilities generally involve the placing of a telephone call or sending a telefax to a medical health facility to determine if a bed or a plurality of beds is available for one or more patients. Further, known methods involve asking a plurality of questions to a representative of the medical health facility to determine types of beds available, types of services offered, payment method accepted and/or other information. These questions must be asked at each facility contacted to determine which facility best suits the patient. Moreover, many times, discharge personnel, doctors and/or nurses must contact the medical health care facilities to gather the information about each facility. This may require discharge personnel, doctors and/or nurses to spend more time performing an administrative task and less time providing care and support to patients and family members often regarding difficult and serious life and/or other health-related decisions.

Further, it is generally known to provide a website having access to a database wherein the database denotes whether beds are available at a healthcare facility. However, known websites and databases do not provide a mechanism for a user to directly contact the healthcare facilities to make appointments, to reserve a bed or beds and/or to gather further information about the facility.

Further, known databases and websites provide no information on the types of beds available, the quantity of beds available and/or a forecast of what beds may be available and when beds may be available in the future. Moreover, known databases and websites do not provide healthcare facilities access to the databases for adding or changing information regarding bed availability.

It is generally known that an ambulance transports an injured patient from, for example, an accident scene or an emergency scene to an emergency room of a hospital for medical treatment. Often, the ambulance at the accident scene or the emergency scene do not know the status of the emergency room of the hospital. Further, the emergency room of the hospital may no longer be accepting new patients and/or a waiting time to the emergency room may jeopardize the health of the injured patient. As a result, the ambulance must transport the injured patient from the hospital to another hospital for medical treatment.

Generally, transporting the injured patient from the hospital to another hospital for medical treatment is known as diverting or bypassing the injured patient to another hospital. If the status of an emergency room of the hospital is unknown, an ambulance with an injured patient may arrive at a full emergency. As a result, the ambulance and/or the injured patient may be diverted or bypassed to another hospital. The diverting or the bypassing of the patient to another hospital for medical treatment causes a delay in time before the injured patient receives medical treatment from a hospital or emergency room. The delay in time increases the risk of death and/or serious injury to the patient. Further, the diverting or the bypassing of the patient increases the amount of work and/or costs associated with transporting of the patient by the ambulance to deliver the patient to a hospital for medical treatment. Further, the increased amount of work by the ambulance reduces the ability of the ambulance to provide services to other injured patients. As a result, the injured patients and/or other injured patients may not receive, timely, necessary medical treatment.

A need, therefore, exists for an improved method and a system for optimizing hospital beds and ambulance allocations via a computer network. Further, a need, exists for an improved method and a system for determining the status of beds in hospitals via a computer network. Still further, a need exists for an improved method and a system for determining the status of the beds in a rooms, such as, for example, an emergency rooms of the hospitals. Moreover, a need exists for an improved method and a system for alert ambulance services of the status of the beds and/or the status of the rooms in the hospitals via the computer network.

SUMMARY OF THE INVENTION

The present invention generally relates to a method and a system for optimizing hospital beds and ambulance allocations via a computer network. More specifically, the present invention generally relates to a method and a system for determining the status of beds and/or rooms in hospitals via a computer network. Further, the present invention relates to a method and a system for determining the status of the beds in rooms of the hospitals and/or the status of the rooms in the hospitals via the computer network. The system and the method may alert ambulance services of the status of the beds in and/or the status of the rooms of the hospitals via the computer network. Still further, the system and the method may reduce the number of patients which must be diverted or bypassed to other hospitals for medical treatment by the ambulance services. Moreover, the system may allow the ambulance to know the status of the beds in the hospital before delivery of an injured patient to the hospital. The system may allow the ambulance to know if beds are available at the hospital. Furthermore, the system allows the hospital to notify the ambulances of the availability of the beds in the hospital.

To this end, in an embodiment of the present invention, a method for delivering a patient to a room in a hospital is provided. The method has the steps of providing a computer network and providing a database connected to the computer network. Further, the method has the step of inputting information into the database by a hospital via the computer network wherein the information is associated with available beds in the room. Still further, the method has the step of providing a first access to the database for viewing the information by a user of the database via the computer network. Moreover, the method has the step of determining a status of the room based on the information in the database. Furthermore, the method has the step of communicating the status of the room to a service provider via the computer network wherein the service provider transports the patient based on the status of the room.

In an embodiment, the computer network is the internet.

In an embodiment, the first access to the database is wireless.

In an embodiment, the method has the step of assigning a color to represent the status of the room.

In an embodiment, the method has the step of updating the information in the database by the hospital via the computer.

In an embodiment, the method has the steps of providing a remote server and storing the database on the remote server.

In an embodiment, the method has the step of inputting a wait time for the room into the database by the hospital via the computer.

In an embodiment, the method has the step of inputting staff information into the database by the hospital via the computer.

In an embodiment, the method has the step of calculating a wait time for the room based on the information in the database.

In an embodiment, the method has the step of notifying the hospital of a patient in route to the room in the hospital via the computer network.

In an embodiment, the method has the step of reporting the status of the room to a manager.

In an embodiment, the first access to the database is a hyperlink in a webpage on the computer network.

In an embodiment, the method has the step of managing the service provider with the information in the database via the computer network.

In another embodiment of the present invention, a system for allocating an available bed in an emergency room to a patient wherein the emergency room has a plurality of beds is provided. The system has a computer network and a database associated with the computer network. Further, the system has a means for inputting information into the database wherein the information is associated with available beds in the plurality of beds. Still further, the system has a means for accessing the information and modifying the information in the database. Moreover, the system has a means for managing the available beds in the emergency room.

In an embodiment, the computer network is the internet.

In an embodiment, the system has a means for determining a status of the emergency room based on the information in the database.

In an embodiment, the system has a color code associated with the available beds in the plurality of beds of the emergency room.

In an embodiment, the system has a remote server wherein the database is contained on the remote server and a website providing access to the database.

In an embodiment, the system has a means for delivering the patient to one of the available beds in the emergency room.

It is, therefore, an advantage of the present invention to provide a system and a method for optimizing hospital beds and ambulance allocations via a computer network.

A further advantage of the present invention is to provide a system and a method for optimizing hospital beds and ambulance allocations via a computer network which allow hospitals and/or ambulance services to warn users of status of beds in the hospitals.

Another advantage of the present invention is to provide a system and a method for optimizing hospital beds and ambulance allocations via a computer network which allow hospitals and/or ambulance services to warn users of status of beds in emergency rooms in the hospitals.

And, another advantage of the present invention is to provide a system and a method for optimizing hospital beds and ambulance allocations via a computer network which provide a warning system with colors representing the status of beds in hospitals.

Yet another advantage of the present invention is to provide a system and a method for optimizing hospital beds and ambulance allocations via a computer network which allow hospitals and/or ambulance services to update the status of beds in the hospital via the computer network.

A further advantage of the present invention is to provide a system and a method for optimizing hospital beds and ambulance allocations via a computer network which allow emergency management personnel to send bulletins and/or alerts to users via the computer network.

A still further advantage of the present invention is to provide a system and a method for optimizing hospital beds and ambulance allocations via a computer network which provide summaries and/or reports to emergency management personnel via the computer network.

Moreover, an advantage of the present invention is to provide a system and a method for optimizing hospital beds and ambulance allocations via a computer network which allow hospitals to provides numbers of patients in waiting rooms and average wait times for waiting rooms in the hospitals to the computer network.

And, another advantage of the present invention is to provide a system and a method for optimizing hospital beds and ambulance allocations via a computer network which allow hospitals to provide numbers of incoming ambulances to the hospitals, estimated arrival times of the incoming ambulances and/or the status of arriving patients to the computer network.

Yet another advantage of the present invention is to provide a system and a method for optimizing hospital beds and ambulance allocations via a computer network to allow hospitals to increase or decrease the patient flow into the hospitals.

Another advantage of the present invention is to provide a system and a method for optimizing hospital beds and ambulance allocations via a computer network which allow ambulances to notify hospitals of incoming patients.

And, another advantage of the present invention is to provide a system and a method for optimizing hospital beds and ambulance allocations via a computer network which allow beds in hospitals to be allocated to ambulances.

Yet another advantage of the present invention is to provide a system and a method for optimizing hospital beds and ambulance allocations via a computer network which allow hospitals to optimize beds in the hospitals for patients and/or ambulance services.

A further advantage of the present invention is to provide a system and a method for optimizing hospital beds and ambulance allocations via a computer network which allow emergency services, fire departments and/or emergency personnel to access the computer network.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention generally relates to a method and a system for optimizing hospital beds and ambulance allocations via a computer network. More specifically, the present invention generally relates to a method and a system for determining the status of beds in hospitals via a computer network. The system and the method may allocate the beds in the hospitals to ambulances and/or ambulance services. Further, the system and the method may optimize the beds in the hospitals by allocating the beds in the hospitals to users of the computer network. Moreover, the system and the method may reduce the number of patients which must be diverted or bypassed to other hospitals for medical treatment.

Figure 1:
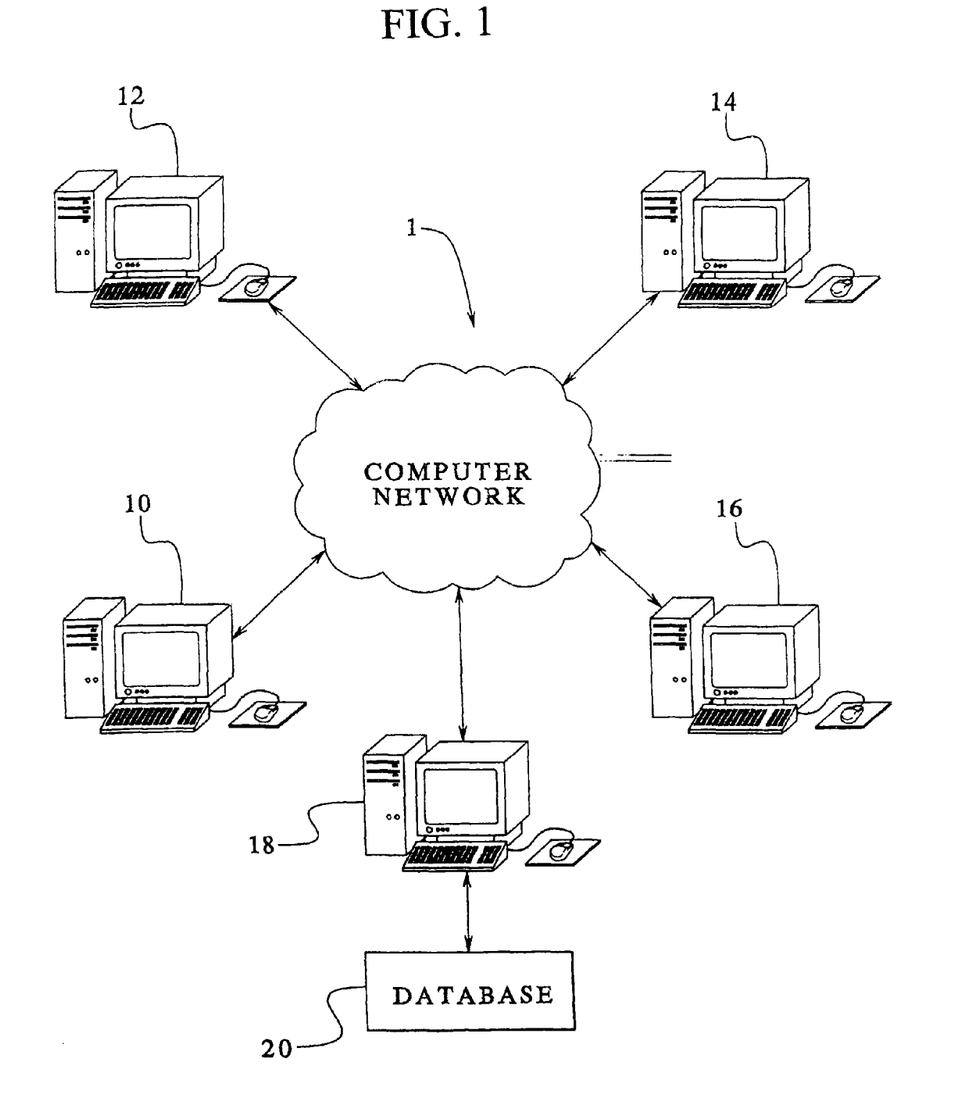
FIG. 1 illustrates a diagram of interconnected computers and a database in an embodiment of the present invention.

Referring now to the drawings wherein like numerals refer to like parts, FIG. 1 illustrates a computer network 1 having a plurality of computers 10-16 connected thereto. Further, the computer network 1 may include one or more server computers 18 having a database 20 attached thereto.

The computer network 1 may be any type of computer network that may interconnect a plurality of computers 10-16. Of course, any number of computers may be connected to the computer network and the invention should not be construed as limited as herein described. Further, the computer network 1 may be, for example, the internet wherein a plurality of remote computers are connected via a telephone network or other like network to each other. In addition, the computer network 10 may be an intranet wherein the plurality of computers 10-16 are connected via a network internal to an organization, such as a business, institution or the like. For example, the network may be connected via a LAN network. However, any computer network may be utilized that may be apparent to those skilled in the art.

The server computer 18 may include the database 20 associated therewith. The database 20 may contain information input into the database relating to bed availability information of healthcare providers. Any healthcare facility having bed availability information may use any of the computers 10-16 or any other computer connected via the computer network 1 to access the database 20 through the computer network 1.

The healthcare facility may then enter the bed availability information into the database 20. A user of the database 20 desiring information concerning the availability of beds in a plurality of healthcare facilities could use any of the computers 10-16 or any other computer to access the database 20 and to extract the information concerning the availability of the beds of any of the healthcare facilities stored therein. The network 1, therefore, allows for real time updates and access to those updates regarding bed availability as a patient is checked in and subsequently checked out of the facility.

Further, any of the computers 10-16 may be a wireless system whereby the computer network may be accessed from a remote location. For example, any of the computers 10-16 may be a Palm Pilot™ by 3Com, Inc. that may access the internet wirelessly. The computers 10-16 may be, for example, a laptop computer, a handheld computer and/or the like. Further, any of the computers 10-16 may be a wireless telephone having access to the internet.

Figure 2:
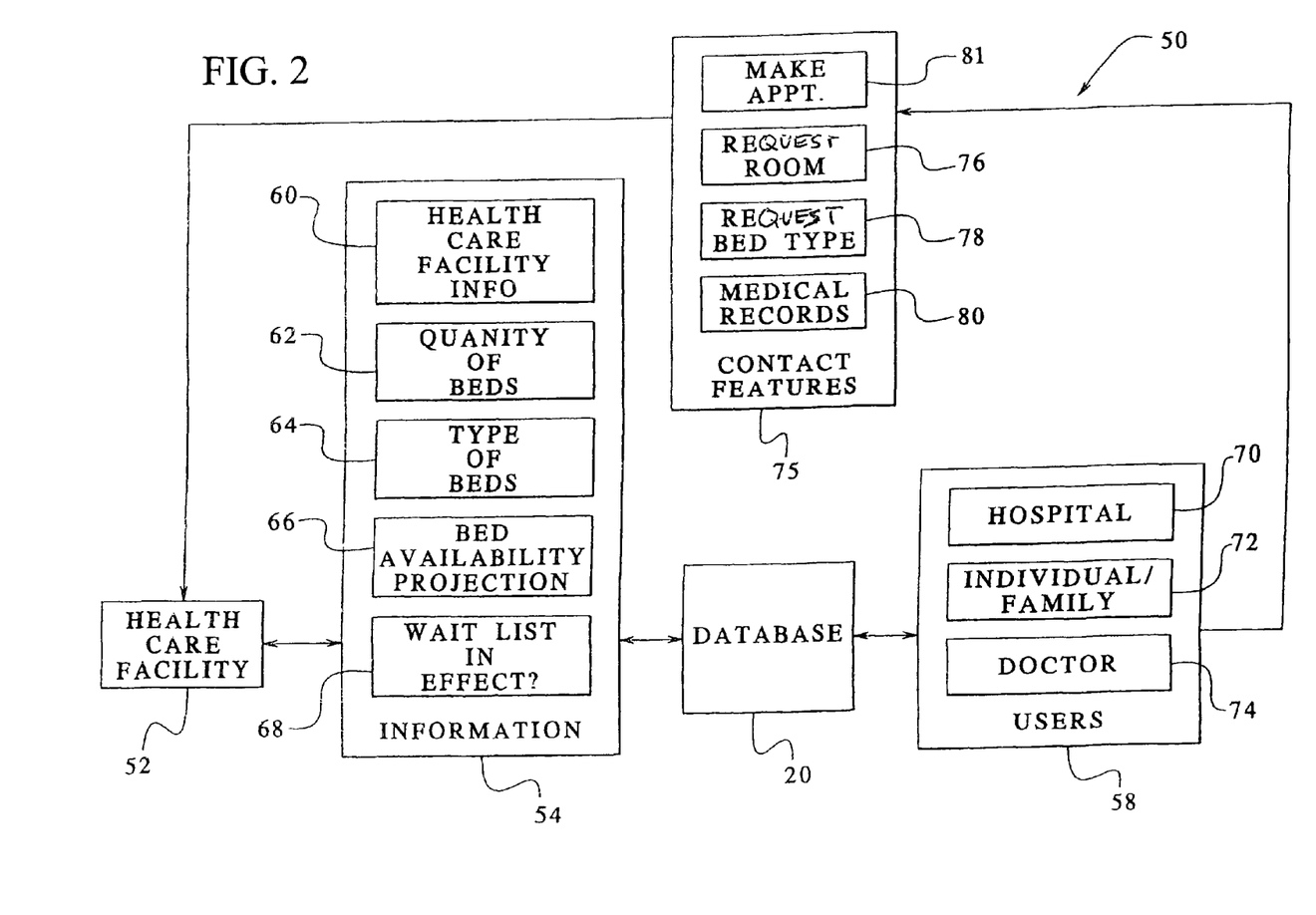
FIG. 2 illustrates a black box diagram of a healthcare provider and information that may be input into the database in an embodiment of the present invention.

FIG. 2 illustrates a black box diagram of a system 50. The system 50 includes a healthcare facility 52. Of course, any number of healthcare facilities may be included in the system 50. The healthcare facility 52 may be any type of healthcare facility, such as, for example, an assisted living facility, a home care facility, a nursing home facility, a geriatric rehabilitation facility, a continuing care facility, a hospice facility and/or a retirement home facility. Further, any other type of healthcare facility may be included in the present invention and is not meant to be limited as herein described.

The healthcare facility 52 may provide information 54 to the database 20 for a plurality of users 58 to download. The information 54 may include healthcare facility information 60, a quantity of beds 62 in the healthcare facility 52, types of beds 64 in the healthcare facility 52, a bed availability projection 66 in the healthcare facility 52 and whether a wait-list 68 is in effect in the healthcare facility 52. Further, any other information may be provided by the healthcare facility 52 to the database 20 as may be apparent to those skilled in the art.

The healthcare facility information 60 may include a map, contact information, details of the healthcare facility 52 and/or a history of the healthcare facility 52. In addition, any other type of information may be provided about the healthcare facility 52 that may be apparent to those skilled in the art to be stored in the database 20.

The types of beds 64 available in the healthcare facility 52 may include any type of bed that the healthcare facility offers, such as, for example, beds suited for Alzheimer's disease patients, beds for intermediate care, beds with ventilators, beds in isolation, beds in negative air isolation, beds for males or females, single beds and/or luxury beds. Of course, other types of beds may be provided by the healthcare facilities that may be apparent to those skilled in the art.

The bed availability projection 66 may provide information concerning what the status of empty beds at a particular healthcare facility 52 may be in the future. For example, if the healthcare facility 52 has every bed full, the healthcare facility 52 may provide information that the a bed or a particular type of bed may be available within, for example, the following seven days. Of course, the bed availability projection 66 may provide information concerning the availability of beds at a healthcare facility for any specified time into the future such as, for example, days or weeks into the future.

The users 58 may have access to the database and may retrieve the information 54 from the database 20. The users may include a hospital 70, an individual or a family 72 and/or physicians 74. However, the users 58 may include anyone who desires to retrieve the information 54 about the healthcare facility 52 from the database 20, and the present invention should not be construed as limited as herein described.

Upon receiving the information 54 about the healthcare facility 52 from the database 20, the user 58 may then contact the healthcare facility 52 via one of the contact features 75. The user 58 may, for example, request a room 76, request a bed type 78, transfer medical records 80 to the healthcare facility 52 and/or make an appointment 81 with the healthcare facility 52. Moreover, the user 58 may contact the healthcare facility 52 for any other reason that may be apparent to those skilled in the art.

The database 20 may be contained on a website or other graphical interface on the computer network that may provide electronic forms for the healthcare facility 52 to enter the information 54 into the database 20 or for the users 58 to obtain the information 54 from the database 20. Further, the healthcare facility 52 or the user 58 may have a website ID number and/or a password to maintain privacy and/or to change and save information input into the database 20 or taken from the database 20. The database 20 may be accessed via a single website or via a plurality of websites that are linked to the database 20.

Figure 3:
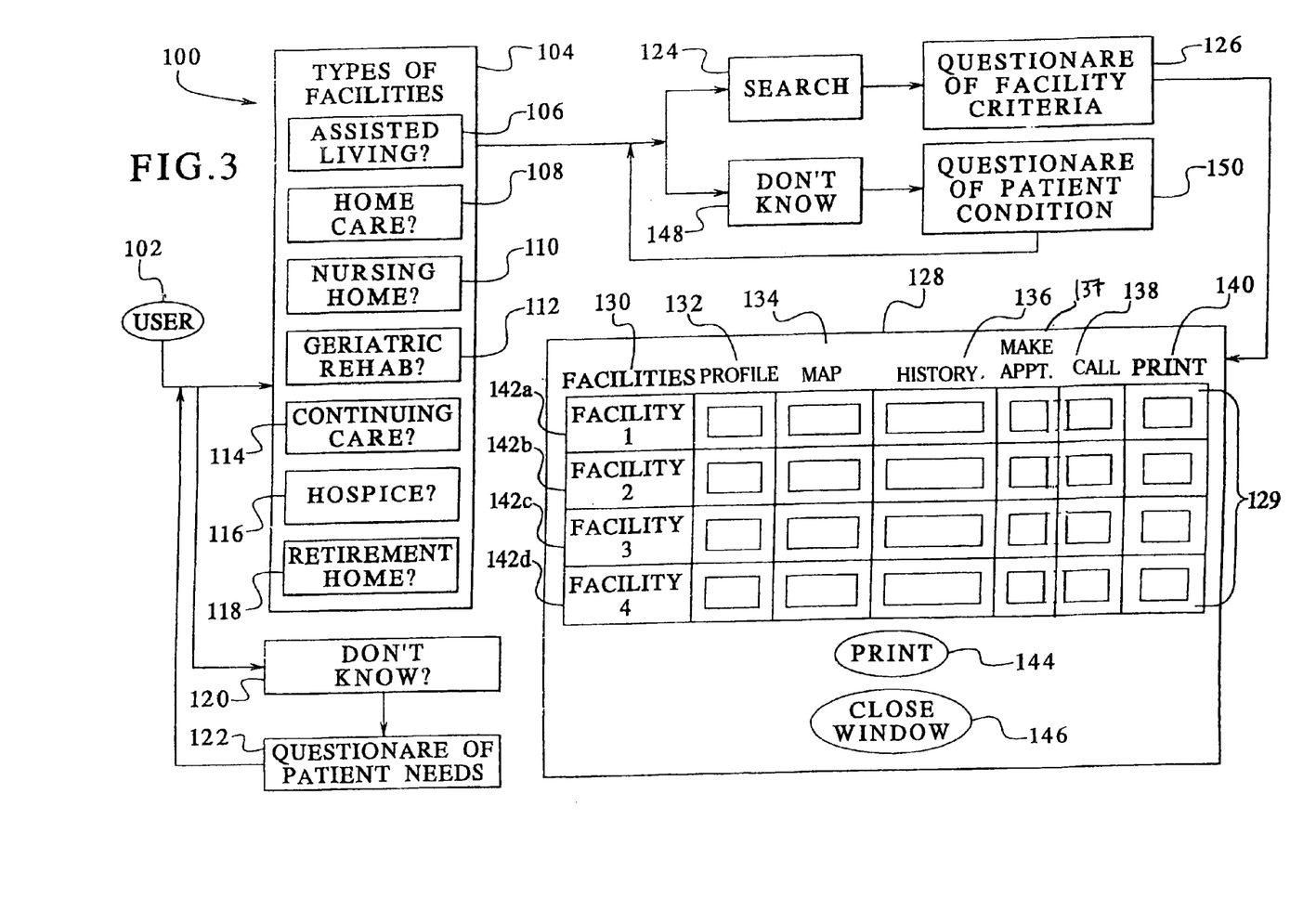
FIG. 3 illustrates a black box diagram of a decision tree and a results screen in an embodiment of the present invention.

FIG. 3 illustrates a navigation tree 100 whereby an individual user 102 may access a website or other graphical interface to begin the process of choosing a healthcare facility. The user 102 may choose from a plurality of types of facilities 104. The types of facilities 104 may include, for example, assisted living facilities 106, home care facilities 108, nursing home facilities 110, geriatric rehabilitation facilities 112, continuing care facilities 114, hospice facilities 116 and/or retirement home facilities 118. Further, any other healthcare facility may be included in the types of facilities 104 that may be apparent to those skilled in the art.

If, however, the user 102 does not know which type of healthcare facility 104 he or she may need, the user 102 may hit a "DON'T KNOW" button 120 within the graphical interface. The "DON'T KNOW" button 120 may then link the user 102 to a questionnaire of patient needs 122 whereby the user 102 answers a plurality of questions regarding the needs of the patient to be placed in the facility. The questionnaire of patient needs 122 may help the user 102 choose a type of facility that may be suited to the patient. Of course, the user 102 may be the patient seeking the type of facility. Alternatively, the user 102 may be an individual helping another in determining what type of facility may be best for the other.

The questionnaire of patient needs 122 may then be analyzed to determine and/or to recommend the type of facility needed by the user 102. The website may then link the user 102 to the particular type of facility that is recommended after answering the questions. Alternatively, the graphical interface may link the user 102 back to the types of facilities 104 thereby presenting the user 102 with the choice of the type of facilities the user 102 may desire.

The user 102 may choose a type of facility best suited for the user 102 or for another. After choosing one of the types of facilities 104, the user 102 may then search the database 20 via a search command 124 to find a particular facility or a plurality of facilities best suited for the user 102. The search command 124 may link the user 102 to a questionnaire of facility criteria 126 having a series of questions designed to find an individual facility or a plurality of facilities that match the particular criteria of the user 102.

For example, the questionnaire of facility criteria 126 may ask the user 102 to narrow the search to a particular geographic area. Further, the user 102 may input other information, such as, for example, concerning the payment method, type of facility, type of ownership, religious affiliation, population served, languages spoken, acceptance criteria, special units needed, service category needed, services needed and/or relationship with other entities. Further, other information may be used to narrow the choice of facility to one or any other number for the user 102 to choose.

After the user 102 inputs information into the questionnaire of facility criteria 126 and submits the information, a results window 128 may appear to show which facilities match the particular criteria of the user 102. The results screen 128 may include a table 129 showing facilities 130, profiles of the facilities 132, a map to the facility 134, a history of the facility 136, an option to make appointment 137, a call option 138 that allows the computer to immediately connect the user 102 to the facility via a telephone or telephone utility contained within the computer, or an option to print the information 140. The results screen 128 may include a facility 1(142a), a facility 2(142b) a facility 3(142c), a facility 4(142d) or any other facility that may be apparent to those skilled in the art that is matched by the search command 124.

The results screen 128 may include a print button 144 that may print the information of the facilities 130 as shown on the results screen 128. Further, the results screen 128 may include a "close window" button 146 that may close the results screen 128 of the graphical interface when the user 102 is finished viewing and/or printing the results screen 128. Still further, the user 102 may save the results of the search to easily access the results at a later time. In addition, the user 102 may compile lists of "favorite" healthcare facilities and save the lists in the database 20 to access at a later time.

Before the user 102 searches the database 20, the user 102 may desire a better understanding of how to match a patient's condition with the facility criteria. Therefore, a "DON'T KNOW" button 148 may be provided that may allow the user 102 to answer a plurality of questions in a questionnaire of patient condition 150. The questionnaire of patient condition 150 may include a plurality of questions related to the condition of the patient. An analysis of the answers to the questionnaire of patient condition 150 may be conducted to indicate to the user 102 what particular criteria the user 102 may be looking for in a particular facility. Further, the website may automatically search the database 20 for matching healthcare facilities based on the answers to the questionnaire of patient condition 150.

As indicated previously, the user 102 may be connected with the particular facility 130 to reserve a room 76, to reserve a bed type 78, to securely send medical records 80 thereto and/or to make an appointment 81 with the facility (as shown in FIG. 2).

Still further, if the user 102 decides to view the details 136 of the facility 130, the details 136 may indicate to the user 102 the quantity of beds provided, the types of bed provided, a bed availability projection or whether a wait-list is in effect for that facility 130. The user 102 may then use this information to find a bed in the particular facility 130 best suited for the user 102.

Figure 4:
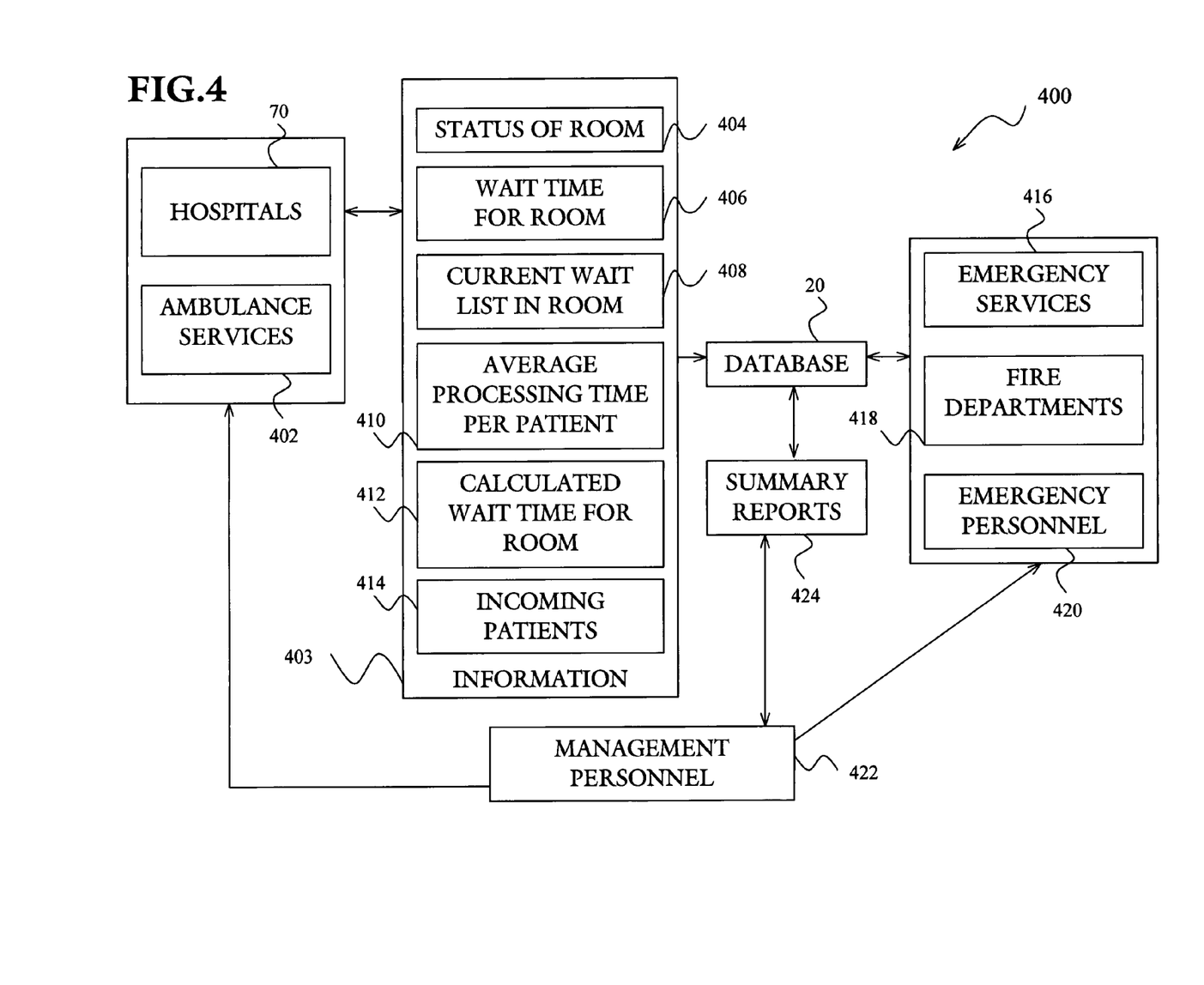
FIG. 4 illustrates a black box diagram of interconnected parties optimizing beds in hospitals and the database in an embodiment of the present invention.

In another embodiment of the present invention, FIG. 4 illustrates a black box diagram of a system 400. The system 400 may include, for example, hospitals 70 and/or ambulance services 402, the emergency services 416, fire departments 418, emergency personnel 420 and/or management personnel 422. The hospitals 70 may provide medical treatment to patients, such as, for example, patients requiring emergency services for injuries cause from medical conditions, accidents, crimes, natural disasters, acts of terrorism, acts of war and/or the like. The patients may have been injured at accident scenes and/or emergency scenes. Each of the accident scenes may have been caused by an accident, such as, for example, an automobile accident, a motorcycle accident, a boat accident, a sporting accident, a gun shooting, a knife stabbing and/or the like. The emergency scenes may have been caused by an emergency, such as, for example, a medical condition, a natural disaster, an act of terrorism, a crime, a fire and/or the like. The hospitals 70 may have emergency rooms to receive and/or to treat the patients. The hospitals 70 may have beds in the emergency rooms for treating the patients. The present invention should not be deemed as limited to the embodiment of a specific accident and/or emergency.

The ambulance services 402 may include an ambulance or ambulances. The ambulance services 402 may be dispatched to the accident scenes and/or the emergency scenes. Personnel of the ambulance services 402 may stabilize the patients at the accident scenes and/or the emergency scenes. The ambulances may transport and/or deliver each of the patients to emergency rooms at one or more of the hospitals 70 to receive medical treatment. The ambulance services 402 may include other vehicles, such as, for example, airplanes, helicopters, ships or any combination thereof. It should be understood that the system 400 may include any number of hospitals 70 and/or ambulance services 402 that may be implemented by one having ordinary skill in the art. The present invention should not be deemed as limited to the embodiments of a specific vehicle provided by the ambulance services 402.

The emergency services 416 may include personnel which may provide services, such as, for example, telephone emergency services, emergency medical services, law enforcement services, national guard services, armed forces, disaster relief services and/or terrorism response services. The fire departments 418 may include firemen, rescue personnel and/or the like. The emergency personnel 420 may include personnel, such as, for example, police officers, emergency medical technicians, nurses, medical assistants, military personnel, rescue personnel and/or humanitarian relief workers. The management personnel 422 may be employees of an entity, such as, for example, a government entity or a public entity. Duties of the management personnel 422 may include, managing and/or directing public services during a time of emergency. The present invention should not be deemed as limited to the embodiment of a specific services of the emergency services 416 and/or a specific personnel of the emergency personnel 420.

As illustrated in FIGS. 1 and 4, the hospitals 70 and/or the ambulance services 402 may provide the information 403 to a database 20 to download via the computer network 1 and/or the plurality of computer 10-16. The database 20 may be programmed to receive the information 403 from the hospitals 70 and/or the ambulance services 402 via the plurality of computers 10-16 and/or the computer network 1. The database 20 may provided websites or other graphical interfaces to the plurality of computers 10-16 via the computer network 1. The database 20 may be programmed to provide electronic forms to the hospitals 70 and/or the ambulance services 402 to enter the information 403 into the database 20 on the computer network 1 via the websites and/or other graphical interface. Further, the database 20 may be programmed to allow the hospitals 70, the ambulance services 402, the emergency services 416, the fire departments 418, the emergency personnel 420 and/or the management personnel 422 to obtain the information 403 from the database 20 on the computer network 1 via the website and/or other graphical interface. Further, the database 20 may be programmed to provide the hospitals 70, the ambulance services 402, the emergency services 416, the fire departments 418, the emergency personnel 420 and/or the management personnel 422 with website ID numbers and/or passwords to maintain privacy and/or to change and save the information 403 input into the database 20 and/or taken from the database 20. The database 20 may be accessed via a single website or via a plurality of websites that are linked to the database 20 by the computer network 1.

As illustrated in FIGS. 1 and 4, the database 20 may be accessed by the hospitals 70, the ambulance services 402, emergency services 416, the fire departments 418, the emergency personnel 420 and/or the management personnel 422 via the computer network 1 which may be any type of computer network that may interconnect the plurality of computers 10-16. Of course, any number of computers may be connected to the computer network and the invention should not be construed as limited as herein described. The computer network 1 may be, for example, the internet wherein a plurality of remote computers are connected via a telephone network or other like network to each other. In addition, the computer network 1 may be an intranet wherein the plurality of computers 10-16 are connected via a network internal to an organization, such as, for example, a business, an institution and/or the like. For example, the network may be connected via a LAN network.

Further, the access to the database 20 via the computer network 1 may be wired access, such as, for example, telephone modem access, cable modem access, DSL access, T1 access and/or the like. Still further, the access to the computer network 1 may be wireless access, such as, for example, wireless Ethernet card access, Wi-Fi access or any wireless access which transmits and receives signals in the radio band. However, any computer network and/or any access to the computer network may be utilized that may be apparent to those skilled in the art.

As illustrated in FIGS. 1 and 4, the hospitals 70 and/or the ambulance services 402 may input the information 403 to the database 20 via the plurality of computers 10-16 and/or the computer network 1. The hospitals 70, the ambulance services 402, emergency services 416, the fire departments 418, the emergency personnel 420 and/or the management personnel 422 may access the computer network 1 with the plurality of computers 10-16 in the hospitals 70, the ambulance services 402, emergency services 416, the fire departments 418, the emergency personnel 420 and/or the management personnel 422, respectively. The database 20 may provide the electronic forms to the hospitals 70 and/or the ambulance services via the computer network 1. The database 20 and/or the electronic forms may be accessed on-line by the plurality of computers 10-16 in the hospitals 70 and/or the ambulance services 402. The hospitals 70 and/or the ambulance services 402 may access the database 20 and/or the electronic forms on the computer network 1 by, for example, opening a hyperlink on the website with one of the plurality of computers 10-16 and/or inputting the website ID numbers and/or the passwords into the website. The emergency services 416, the fire departments 418, the emergency personnel 420 and/or the management personnel 422 may access the database 20 on the computer network 1 by, for example, opening a hyperlink on the website with one of the plurality of computers 10-16 and/or inputting the website ID numbers and/or the passwords into the website.

The information 403 may include information relating to the status of the beds in the rooms in the hospitals 70 and/or the status of the rooms of the hospitals 70. Further, the information 403 may include information relating a room, such as, for example, an emergency room in each of the hospitals 70. Still further, the information 403 may include information relating to a status of a room 404 in the each of the hospitals 70, a wait time for a room 406 in each of the hospitals 70, an average processing time per patient 410 in each of the hospitals 70, a calculated wait time for a room 412 in each of the hospitals 70 and/or incoming patients 414 in each of the hospitals 70. The information 403 may be automatically entered into the database 20 and/or the electronic forms, for example, by one of the plurality of computers 10-16 in the hospitals 70 and/or the ambulance services 402 via the computer network 1. Alternatively, the patient information 403 may be manually entered into the database 20 and/or the electronic forms by personnel of the hospitals 70 and/or the ambulance services 402 via one of the plurality of computers in the hospitals 70 and/or the ambulance services 402, respectively, on the computer network 1.

The status of room 404 may include information relating to the status of the beds in the hospitals 70 or the status of rooms, such as, for example, emergency rooms in the hospitals 70. The status of the room 404 may be, for example, accepting patients, reaching capacity and/or not accepting patients. The database 20 may be programmed to assign a color to represent the status of the room 404. The database 20 may display the information 403 on the website or the websites accessible by the plurality of computers 10-16 via the computer network 1. The information 403 and/or the status of the room 404 for each of the hospitals 70 may be displayed in the color corresponding to the status of the rooms in each of the hospitals 70 on the website or the websites via the plurality of computers 10-16. The color may be, for example, green, orange or red. For example, green may indicate that the room of one of the hospitals may be accepting patients, orange may indicate that the room of one of the hospitals 70 may be reaching capacity or red may indicate that the room of one of the hospitals may not be accepting patients. The status of the room 404 may be updated by the hospitals 70 and/or the ambulance services 204 via the plurality of computers 10-16 and/or the computer network 1. As a result, the color may change to indicate a current status of the rooms of the hospitals 70. The status of the room 404 and/or the color for each of the hospitals 70 may be stored in the database 20. The present invention should not be deemed as limited to the embodiment of a specific color of the status of room 404 and/or the information 403.

Parameters may be programmed into and/or stored in the database 20. The parameters may automatically change the status of the room 404 and/or the color for each of the hospitals 70. The database 20 may store the status of the room 404 and/or the color therein. The rooms of the hospitals 70 may accept or may process patients which may change the status of the beds and/or the status of the rooms of the hospitals 70. The hospitals 70 and/or the ambulance services 202 may change the status of the rooms 404 and/or the color stored in the database 20 to indicate the currents status of the beds and/or the status of the rooms of the hospitals 70. The hospitals 70 and/or the ambulance services 402 may access the database 20, may change the status of the room 404 and/or the color in the database and/or may store the status of the room 404 and/or the color in the database via the plurality of computers 10-16 and/or the computer network 1.

The hospitals 70 and/or the ambulance services 402 may control a number of patients being transported to the hospitals 70 by changing the status of the rooms 404 in the database 20. The hospitals 70 and/or the ambulance services 402 may increase the number of patients being transported to the hospitals 70 by changing the status of the rooms 404 to indicate that the hospitals 70 are accepting patients. The hospitals 70 and/or the ambulance services 402 may decrease the number of patients being transported to the hospitals 70 by changing the status of the rooms 404 to indicate that the hospitals 70 are reaching capacity. The hospitals 70 and/or the ambulance services 402 may prevent patients from being transported to the hospitals 70 by changing the status of the rooms 404 to indicate that the hospitals 70 are not accepting patients.

The information 403 may include number of beds available for patients in the emergency rooms of the hospitals 70. Still further, the information 403 may include numbers of beds occupied by patients in the emergency rooms of the hospitals 70. The hospitals 70 may update the status of room 404 stored in the database 20 via the computer network 1 to indicate the current status of the hospitals 70.

The wait time for the room 406 may include wait times for the emergency rooms of the hospitals 70. The wait times may indicate how long of time a patient will wait in the emergency rooms before receiving medical treatment in the emergency rooms. The wait times for the emergency rooms may increase or decrease based on the number of patients awaiting medical treatment in the emergency rooms. The wait times for the emergency rooms may increase or decrease based on the number of patients expected to arrive. The hospitals 70 and/or the ambulance services 202 may access the wait time for the room 406 in the database 20 via the plurality of computers 10-16 and/or the computer network 1. The hospitals 70 and/or the ambulance services 202 may change the wait time for the room 406 in the database 20 to indicate the current wait times in the emergency rooms in the hospitals 70 via the plurality of computers 10-16. The hospitals 70 and/or the ambulance services 202 may store the wait time for the room 406 in the database 20.

The current wait list in the room 408 may include numbers of patients in the emergency rooms of the hospitals 70 awaiting medical treatment. The current wait time for the room 408 may indicate the number of patients waiting in the emergency rooms to receive medical treatment in the emergency rooms. The number of patients waiting in the emergency rooms may increase or decrease based on the number of patients being transported to the emergency rooms and durations of time that the patients remain in the emergency rooms. The hospitals 70 and/or the ambulance services 202 may access the current wait list in the room 408 in the database 20 via the plurality of computers 10-16 and/or the computer network 1. The hospitals 70 and/or the ambulance services 202 may change the current wait list in the room 408 in the database 20 to indicate the current wait list in the emergency rooms in the hospitals 70 via the plurality of computers 10-16. The hospitals 70 and/or the ambulance services 202 may store the current wait list in the room 406 in the database 20.

The average processing time per patient 410 may include average times to process each of the patients in the emergency rooms of the hospitals 70. The average times may be calculated by the personnel of the hospitals 70 and/or the ambulance services 202 via the plurality of computers 10-16. The average times for the emergency rooms may increase or decrease based on personnel of the hospitals 70 providing medical treatment to the patients of the emergency rooms and/or the injuries of the patients accepted by the emergency rooms of the hospitals 70. The hospitals 70 and/or the ambulance services 202 may access the average processing time per patient 410 in the database 20 via the plurality of computers 10-16 and/or the computer network 1. The hospitals 70 and/or the ambulance services 202 may change the average processing time per patient 410 in the database 20 to indicate the current average times to process patients of the emergency rooms in the hospitals 70 via the plurality of computers 10-16. The hospitals 70 and/or the ambulance services 202 may store the average processing time per patient 410 in the database 20.

The calculated wait time for the room 412 may include wait times that patients of the emergency rooms may anticipate before receiving medical treatment in the emergency rooms of the hospitals 70. The wait times are based on the number of patients awaiting treatment in the emergency rooms and the average times to process each of the patients in the emergency rooms of the hospitals 70. The wait times for the emergency rooms may increase or may decrease based upon the number of patients awaiting medical treatment in the emergency rooms of the hospitals 70 and/or the number of expected arriving patients. The hospitals 70 and/or the ambulance services 202 may access the calculated wait time for the room 412 in the database 20 via the plurality of computers 10-16 and/or the computer network 1. The hospitals 70 and/or the ambulance services 202 may change the calculated wait time for the room 412 in the database 20 to indicate the current wait times in the emergency rooms of the hospitals 70 via the plurality of computers 10-16. The hospitals 70 and/or the ambulance services 202 may store the calculated wait time for the room 412 in the database 20.

The incoming patients 414 may include numbers of patients enroute to the emergency rooms of the hospitals 70 via the ambulance services 402. The numbers of patients enroute to the emergency rooms may increase or decrease based on numbers of patients that suffered injuries at accident scenes and/or emergency scenes. The hospitals 70 and/or the ambulance services 202 may access the incoming patients 414 in the database via the plurality of computers 10-16 and/or the computer network 1. The hospitals 70 and/or the ambulance services 202 may change the incoming patients 414 in the database 20 to indicate the current number of patients enroute to the hospitals 70 via the plurality of computers 10-16. The hospitals 70 and/or the ambulance services 202 may store information relating to the incoming patients 414 in the database 20.

The information 403 may include a status of the ambulance services 402. The status of the ambulance services 202 may be, for example, available to respond, responding to the emergency and/or unable to immediately respond. The ambulance services 402 may access the information 403 in the database 20 via the plurality of computers 10-16 and/or the computer network 1. The ambulance services 202 may select and/or may change the status of the ambulance services 202. The ambulance services 202 may store the status of the ambulance services 202 in the database 20. The present invention should not be deemed as limited to the embodiment of a specific status of the ambulance services 402.

The database 20 may be programmed to generate an alert message concerning the information 403 of the hospitals 70. The database 20 may be programmed to send the alert message to the hospitals 70, the ambulance services 402, the emergency services 416, the first departments 418, the emergency personnel 420 and/or the management personnel 422 via the computer network 1 by, for example, electronic mail services, wireless pager services and/or the like. The hospitals 70, the ambulance services 402, the emergency services 416, the first departments 418, the emergency personnel 420 and/ or the management personnel 422 may access and/or may view the alert message including the information 403 in the database 20 via the computer network 1. As a result, the ambulance services 402, the emergency services 416, the first departments 418, the emergency personnel 420 and/or the management personnel 422 may determine which of the emergency rooms of the hospitals 70 are accepting patients.

The database 20 may be programmed to generate summary reports 424 concerning the information 403 of the hospitals 70. The database 20 may be programmed to send the summary reports 424 to the management personnel 422 via the computer network 1 by, for example, the electronic mail services, the wireless pager services and/or the like. The management personnel 422 may access and/or may view the summary reports 424 including the information 403 in the database 20 via the computer network 1. As a result, the management personnel 422 may determine which of the emergency rooms of the hospitals 70 are accepting patients. The summary reports 424 may indicate which of the hospitals 70 may receive a patient and/or may be capable to provide timely medical treatment to the patient. Further, the summary reports 424 may include the status of the emergency rooms of each of the hospitals 70. Still further, the summary reports 424 may indicate which of the hospitals 70 have incoming injured patents enroute.

Management personnel 422 may review the summary reports 424 and/or may decide to send the patients to one or more of the hospitals 70 for medical treatment. The management personnel 422 may send a bulletin to the hospitals 70, the ambulance services 402, the emergency services 416, the fire departments 418 and/or the emergency personnel 420 via the computer network 1 by, for example, the electronic mail services, the wireless pager services and/or the like. The bulletin may include the information. Further, the bulletin may indicate which of the hospitals 70 may receive injured patients from the ambulance services 402. Still further, the bulletin may direct and/or may order the ambulance services 402, the emergency services 416, the fire departments 418 and/or the emergency personnel 420 to transport the patients to one or more of the hospitals 70. Moreover, the bulletin may notify the hospitals 70 that may be receiving the patients from the ambulance services 402, the emergency services 416, the fire departments 418 and/or the emergency personnel 420. As a result, the management personnel may allocate one or more of the hospitals 70 to the patients transported by the ambulance services 402, the emergency services 416, the fire departments 418 and/or the emergency personnel 420. Furthermore, the beds of the emergency rooms in the hospitals 70 may be optimized to receive a maximum number of patients from the ambulance services 402, the emergency services 416, the fire departments 418 and/or the emergency personnel. As a result, the emergency rooms of the hospitals 70 may provide medical treatment to all of the patients. Moreover, it should be understood that the system 400 may include the information 403 for any number of hospitals 70 and/or ambulance services 402. The database 20 and/or the computer system 1 may display the information 403 for the hospitals 70, for a group of the hospitals 70 and/or for each one of the hospitals 70.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A method for facilitating personnel of an ambulance with a delivery of a patient in the ambulance to a room in a hospital using a computer network and a database connected to the computer network, the method comprising the steps of:

inputting a status of the room into the database wherein the status of the room indicates an availability of the room to receive the patient;

inputting a wait time for the room into the database wherein the wait time indicates a length of time the patient will wait to receive medical treatment in the room;

inputting a processing time into the database wherein the processing time indicates an average length of time required to process the patient at the hospital;

inputting information about the patient into the database;

making a determination to deliver the patient to the room based upon the status of the room, the wait time, the processing time and the information about the patient;

communicating the determination to the personnel of the ambulance wherein the personnel of the ambulance transport the patient based on the determination; and changing the status of the room in the database based on the determination.

2. The method of claim 1 further comprising the step of: providing a first access to the database to the personnel of the ambulance.

3. The method of claim 1 further comprising the step of: communicating the determination to the hospital.

4. The method of claim 1 further comprising the step of: assigning a color to represent the status of the room.

5. The method of claim 1 further comprising the step of: updating the information about the patient in the database by the personnel of the ambulance.

6. The method of claim 1 further comprising the step of: remotely accessing the database.

7. The method of claim 1 further comprising the step of: calculating the wait time for the room based on the length of time the patient will wait to receive medical treatment in the room.

8. The method of claim 1 further comprising the step of: inputting a wait list into the database wherein the wait list indicates a number of patients in the hospital awaiting medical treatment.

9. The method of claim 1 further comprising the step of: calculating the processing time for the patient based on the average length of time required to process the patient at the hospital.

10. The method of claim 1 further comprising the step of: generating a report wherein the reports summarizes the status of the room, the wait time, the processing time and the information about the patient.

11. The method of claim 1 further comprising the step of: updating the status of the room in the database based on an availability of the room to receive the patient.

12. The method of claim 1 further comprising the step of: accessing the database with a hyperlink in a webpage on the computer network.

13. The method of claim 1 further comprising the step of: updating the wait time in the database based on the length of time the patient will wait to receive medical treatment in the room.

14. The method of claim 1 further comprising the step of: updating the processing time in the database based on the average length of time required to process the patient at the hospital.

15. A system for allocating a room from a plurality of rooms in a hospital to a patient in an ambulance based upon healthcare services required by the patient wherein the room is necessary to provide the healthcare services to the patient, the system comprising:

a computer network;

a database associated with the computer network;

means for inputting information into the database wherein the information is associated with the room and further wherein the information indicates a status of the room wherein the status of the room is an availability of the room to receive the patient wherein the information indicates a wait time for the room wherein the wait time is a length of time the patient will wait to receive the healthcare services in the room wherein the information indicates a processing time wherein the processing time is an average length of time required to process the patient at the hospital and further wherein the information indicates the healthcare services required by the patient wherein the database matches the room to the patient based upon the information in the database wherein the patient is delivered to the hospital based on the information in the database wherein the information in the database is accessed via the computer network;

a plurality of computers connected to the computer network to access the information in the database via the computer network wherein one of the plurality of computers is located within the ambulance wherein another of the plurality of computers is located within the hospital; and reports generated by the database from the information wherein the reports summarize the information wherein the reports are accessible by the plurality of computers via the computer network.

16. The system of claim 15 further comprising:

means for providing a bulletin to the ambulance wherein the bulletin directs delivery of the patient to the hospital.

17. The system of claim 15 further comprising:

means for updating the information in the database from the ambulance.

18. The system of claim 15 further comprising:

a code associated with the room wherein the code is a color.

19. The system of claim 15 further comprising:

a remote server located outside of the hospital wherein the database is contained on the remote server; and a website providing access to the database.

20. The system of claim 15 further comprising:

means for providing a bulletin to the hospital wherein the bulletin indicates the room that will receive the patient.

* * * * *